United States Patent [19]

Naumann et al.

[11] Patent Number: 4,822,912

[45] Date of Patent: Apr. 18, 1989

[54] PROCESS FOR THE PREPARATION OF 2,3,5,6-TETRAFLUOROBENZOIC ACID

[75] Inventors: Klaus Naumann, Leverkusen; Rudolf Braden, Odenthal; Heinz Ziemann, Leichlingen, all of Fed. Rep. of Germany

[73] Assignee: Bayer Aktiengesellschaft, Leverkusen, Fed. Rep. of Germany

[21] Appl. No.: 154,270

[22] Filed: Feb. 10, 1988

[30] Foreign Application Priority Data

Feb. 20, 1987 [DE] Fed. Rep. of Germany ....... 3705410

[51] Int. Cl.$^4$ .............................................. C07C 63/04
[52] U.S. Cl. .................................................... 562/493
[58] Field of Search ......................................... 562/493

[56] References Cited

FOREIGN PATENT DOCUMENTS 60-258143 12/1985 Japan ..................... 562/493
61-36244  2/1986 Japan ..................... 562/493

OTHER PUBLICATIONS

Vysochin et al, *Chemical Abstracts*, vol. 71, No. 112563h (1969).
Patent Abstracts of Japan, Band 10, No. 131 (C-346) [2188], 15. Mai 1986; & JP-A-60 258 143 (Nippon Shokubai Kagaku Kogyo K.K.) 20-12-1985.

*Primary Examiner*—Bruce D. Gray
*Attorney, Agent, or Firm*—Sprung Horn Kramer & Woods

[57] ABSTRACT

2,3,5,6-Tetrafluorobenzoic acid is prepared by hydrogenolysis of pentafluorobenzoic acid (esters).

12 Claims, No Drawings

PROCESS FOR THE PREPARATION OF 2,3,5,6-TETRAFLUOROBENZOIC ACID

The invention relates to a new process for the preparation of 2,3,5,6-tetrafluorobenzoic acid.

2,3,5,6-Tetrafluorobenzoic acid is a known compound which can be used, for example, for the preparation of highly active insecticides (see, for example, DE-OS (German Published Specification) 2,658,074).

There has therefore been no lack of attempts to find suitable processes for the preparation of this compound. However, the processes known hitherto for the preparation of 2,3,5,6-tetrafluorobenzoic acid have severe disadvantages, in particular when carried out on an industrial scale. For example, these processes require poorly accessible starting materials, reactions which are difficult to carry out on a relatively large scale, chemicals which are difficult tp handle on an industrial scale and/or proceed with little selectivity (see, for example, R. J. Harper et al., J.O.C. 29, 2385-2389 (1964); V. I. Vysocin et al., Zh. Obsh. Chim. 39, 1607-1615 (1969); G. G. Ykobson et al., Zh. Org. Khim. 10, 799-804 (1974); EP-A 0 060 617; D. J. Alsop et al., J. Chem. Soc. 1962, 1801-1805).

A process has now been found for the preparation of 2,3,5,6-tetrafluorobenzoic acid that does not have the disadvantages mentioned of the known processes, but instead permits the acid to be prepared from an easily accessible starting material in a simple reaction which can easily be carried out, even on an industrial scale. This process proceeds from pentafluorobenzoic acid. A process for the preparation of this starting material is described, for example, in DE-OS (German Published Specification) 3,104,259.

Surprisingly, it has been found that the fluorine atom in the 4-position of pentafluorobenzoic acid and the esters thereof can be cleaved off with high selectivity by hydrogenolysis. The course of this reaction is surprising since it is known that, as a substituent in aromatic rings, fluorine cannot be cleaved off hydrogenolytically under usual catalytic hydrogenation conditions and that the fluorine atom in the 2-position is removed on reduction of pentafluorobenzoic acid using complex hydrides.

The invention therefore relates to a process for the preparation of 2,3,5,6-tetrafluorobenzoic acid, which is characterized in that pentafluorobenzoic acid, or an ester thereof, is hydrogenated in the presence of conventional hydrogenation catalysts.

The hydrogenation may be carried out, if appropriate, in an organic solvent which is inert under the hydrogenation conditions, for example aromatic or cycloaliphatic hydrocarbons, ethers, esters, amides or alcohols or alternatively in water.

Possible hydrogenation catalysts are the metals palladium, cobalt, nickel, rhodium, ruthenium, iridium and/or rhenium, in metallic or oxidic form, as a solid or deposited on a catalyst support. Palladium-containing catalysts have proven particularly successful.

The hydrogenation of pentafluorobenzoic acid or esters thereof is preferably carried out in the presence of a base in order to bind the hydrogen fluoride produced during the hydrogenation.

Possible bases are both organic and inorganic bases, organic bases which may be mentioned as examples are tertiary amines and inorganic bases are, above all, the hydroxides, oxides and salts of weak acids of the metals of the first, second and third main groups and the second subgroup of the periodic table of the elements. The hydroxides, oxides and salts of sodium, potassium, calcium, magnesium, zinc and aluminium are preferably used. Sodium hydroxide solution, potassium hydroxide solution, sodium carbonate, zinc carbonate and sodium acetate have proven particularly successful as bases.

The bases are generally employed in an amount from 0.9 to 1.5, preferably 0.9 to 1.1 equivalents per mole of pentafluorobenzoic acid ester during the hydrogenolysis of pentafluorobenzoic acid esters, and in an amount from 1.8 to 3.0, preferably 1.8 to 2.1 equivalents per mole of pentafluorobenzoic acid during the hydrogenolysis of pentafluorobenzoic acid.

The hydrogenation of pentafluorobenzoic acid can be carried out at atmospheric pressure or superatmospheric pressure. The hydrogenation is preferably carried out at a hydrogen pressure from 2 to 100 bar, particularly preferably at a hydrogen pressure from 5 to 60 bar.

Depending on the activity of the catalyst used, the hydrogenation is carred out at temperatures from 0° to 180° C., preferably at temperatures from 20° to 120° C.

The reaction temperature is preferably selected so that the hydrogenation proceeds rapidly and is complete within a limited time, for example 10 to 200 minutes, preferably 30 to 120 minutes.

The hydrogenation can be carried out continuously and batchwise. The sequence in which pentafluorobenzoic acid, catalyst, base and, if appropriate, solvent are introduced into the reactor is optional; it may be advantageous to first introduce the catalyst and pentafluorobenzoic acid into the solvent and then to add the base; however, it may also be favourable to introduce the catalyst, the base and, if appropriate, a solvent into the reactor and then to add the pentafluorobenzoic acid.

It has furthermore been found that the selectivity of hydrogenolysis of pentafluorobenzoic acid (esters) can be improved when the hydrogenation is carried out not using the theoretically necessary amount of hydrogen—this is 1 mole of $H_2$ per mole of acid (ester)—or an excess of $H_2$, but instead using less than the stoichiometrically necessary amount of $H_2$, for example using only 0.9 to 0.98 mole of $H_2$ per mole of pentafluorobenzoic acid (ester). Through hydrogenolysis using a deficiency of $H_2$, the formation of interfering by-products which are difficult to remove is avoided.

This is because it has furthermore been found that the crude 2,3,5,6--tetrafluorobenzoic acid produced on hydrogenolysis using a deficiency of $H_2$ can be freed in a simple manner from the pentafluorobenzoic acid which it contains when the crude tetrafluorobenzoic acid (esters) is (are) firstly treated with an alkali metal sulphide and subsequently with an oxidant.

In order to isolate the crude 2,3,5,6-tetrafluorobenzoic acid from the reaction mixture produced on hydrogenation, the catalyst is initially removed, and the liquid phase is then acidified. The liquid phase is worked up in a fashion which is known per se.

The crude tetrafluorobenzoic acid is purified by treatment with the aqueous solution of an alkali metal sulphide at elevated temperature, preferably the boiling temperature of the mixture. Alkali metal sulphides which are preferably used are sodium sulphide and sodium hydrogen sulphide. The amount of alkali metal sulphide depends on the amount of unreacted pentafluorobenzoic acid contained in the crude tetrafluorobenzoic acid. This amount can be determined by high-pressure liquid chromatography (HLPC). 1 mole of alkali metal sulphide is required per mole of pentafluorobenzoic acid; however, the alkali metal sulphide is preferably used in a certain excess so that 1 to 4 moles, preferably 1.5 to 3 moles, of alkali metal sulphide are present per mole of pentafluorobenzoic acid.

The alkali metal sulphides are preferably used in the form of an aqueous solution; the concentrations of these solutions are 0.1 to 50% by weight, preferably 1–10% by weight.

The amount of oxidant which is added to the alkaline mixture present after warming the crude 2,3,5,6-tetrafluorobenzoic acid with the alkali metal sulphide solution also depends on the amount of pentafluorobenzoic acid contained in the crude tetrafluorobenzoic acid; to be precise, three oxidation equivalents are required per mole of pentafluorobenzoic acid; the oxidants are preferably used in a certain excess; for example in an amount such that 3.1–5 oxidation equivalents are present per mole of pentafluorobenzoic acid.

The following oxidants may be mentioned as examples: permanganate, hydrogen peroxide, chromic acid and hypochlorites. Sodium hypochlorite solution is preferably used.

The oxidation reaction is carried out at temperatures from 0° to 100° C., preferably 20° to 60° C.

The 2,3,5,6-tetrafluorobenzoic acid is isolated from the alkaline solution by acidifying these solutions and extracting the acidic solutions with a water-immiscible organic solvent, for example ether. The 4-carboxytetrafluorobenzenesulphonic acid remains in the aqueous solution.

EXAMPLE 1

(a) 53 g of pentafluorobenzoic acid (0.25 mol) are dissolved in 400 ml of water with 53 g of sodium carbonate (0.5 mol). 3.5 g of palladium on charcoal (5%) are added to the solution, which is subsequently hydrogenated in an autoclave for 6 hours at 90° C. and at a hydrogen pressure from 10 to 15 bar.

The catalyst is removed from the reaction solution, and the reaction solution is acidified to a pH of 1 using concentrated hydrochloric acid. The deposited crystals are filtered off under suction. The aqueous filtrate is extracted with ether, and the ether extracts are evaporated to dryness in vacuo. The catalyst is boiled with 50 ml of 5% sodium hydroxide solution; the pH of the filtrate is adjusted to 1 using concentrated hydrochloric acid, and the filtrate is extracted with ether. The combined ether extracts are likewise evaporated in vacuo.

In this fashion, a total of 49.8 g of crude (91% purity) 2,3,5,6-tetrafluorobenzoic acid are obtained (=93.3% of theory).

Melting point: 144°–146° C.

(b) 21 g of this crude tetrafluorobenzoic acid are dissolved in 200 ml of water with 0.3 mol of sodium bicarbonate and 0.05 mol of sodium sulphide. The solution is heated at the boiling temperature for 15 hours. The reaction mixture is subsequently cooled, and 34 g of sodium hypochlorite (content of free chlorine: 13% by weight) are added. The mixture is stirred at room temperature for 1 hour, then acidified to a pH of 1 using concentrated hydrochloric acid, and extracted with ether. After evaporating the ether extracts, 19 g of 2,3,5,6-tetrafluorobenzoic acid (96% pure product; content of pentafluorobenzoic acid <0.05% by weight) are obtained.

Melting point 146° C.

EXAMPLE 2

53 g (0.25 mol) of pentafluorobenzoic acid and 49 g of triethylamine are dissolved in 300 ml of water, and 10 g of Raney nickel are added to the solution. The hydrogenation mixture is hydrogenated in an autoclave for 4 hours at 60° C. and at a hydrogen pressure of 50 bar.

The reaction mixture is acidified to a pH of 1 using concentrated hydrochloric acid. The acidified mixture is worked up as described in Example 1 a).

Yield 50.3 g (purity according to HPLC: 87%)=90% of theory.

Melting point: 132°–134° C.

EXAMPLE 3

4780 g (22.5 mol) of pentafluorobenzoic acid, 27 litres of water, 1804 g of sodium hydroxide and 287 g of palladium catalyst (5% by weight of Pd on activated charcoal) are introduced into an autoclave. The mixture is hydrogenated for 1 hour at 120° C. and a hydrogen pressure of 50 bar.

The hydrogenation mixture is subsequently acidified to a pH of 1 using concentrated hydrochloric acid, and worked up as described in Example 1 a).

Yield: 4.326 g (89% of theory; purity according to HPLC: 90%).

Melting point: 139°–141° C.

What is claimed is:

1. A process for the preparation of 2,3,5,6-tetrafluorobenzoic acid comprising hydrogenating pentafluorobenzoic acid or an ester thereof in the presence of a hydrogenation catalyst, a base, and a solvent at a pressure of 2 to 100 bars, wherein 0.9 to 0.98 moles of hydrogen are employed per mole of pentafluorobenzoic acid wherein the catalyst is selected from the group consisting of palladium, cobalt, nickel, rhodium, ruthenium, iridium, rhenium and mixtures thereof, in metallic or oxidic form.

2. A process according to claim 1 in which the hydrogenation catalyst used is a palladium-containing catalyst.

3. A process according to claim 1 in which the base used is selected from the group consisting of sodium hydroxide and sodium carbonate.

4. A process according to claim 1 in which the solvent used is water.

5. A process according to claim 1 further comprising treating the crude 2,3,5,6-tetrafluorobenzoic acid obtained from the hydrogenation firstly with an alkali metal sulphide and subsequently with an oxidant to obtain purified 2,3,5,6-tetrafluorobenzoic acid.

6. A process according to claim 5 in which the reaction with the alkali metal sulphide and the oxidant is carried out in aqueous solution.

7. A process according to claim 5 in which the alkali metal sulphide is used in an amount which corresponds to the amount of unreacted starting compound.

8. A process according to claim 1, wherein the pressure is 5 to 60 bars.

9. A process according to claim 1, wherein the temperature is 20° C. to 120° C.

10. A process according to claim 1, wherein the process is conducted for 10 to 200 minutes.

11. A process according to claim 1, wherein the process is conducted for 30 to 120 minutes.

12. A process according to claim 1, wherein the solvent is an organic solvent.

* * * * *